(12) United States Patent
Schultz et al.

(10) Patent No.: US 9,741,104 B2
(45) Date of Patent: Aug. 22, 2017

(54) APPARATUS, METHOD, AND COMPUTER-READABLE MEDIUM FOR QUAD RECONSTRUCTION USING HYBRID FILTER CONVOLUTION AND HIGH DYNAMIC RANGE TONE-MAPPING

(71) Applicant: TOSHIBA MEDICAL SYSTEMS CORPORATION, Otawara-shi (JP)

(72) Inventors: Kurt Walter Schultz, North Providence, RI (US); Steven Reynolds, North Providence, RI (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/715,237

(22) Filed: May 18, 2015

(65) Prior Publication Data

US 2016/0343117 A1     Nov. 24, 2016

(51) Int. Cl.
*G06K 9/00* (2006.01)
*G06T 5/00* (2006.01)
(Continued)

(52) U.S. Cl.
CPC ............. *G06T 5/009* (2013.01); *G06T 5/20* (2013.01); *G06T 11/005* (2013.01); *G06T 11/60* (2013.01);
(Continued)

(58) Field of Classification Search
CPC .... H04N 5/142; H04N 5/23254; H04N 5/217; H04N 9/646; H04N 19/513; H04N 5/2355; H04N 19/176; G06T 2207/10024; G06T 5/001; G06T 7/408; G06T 19/00; G06T 2210/41; G06T 2207/10072;
(Continued)

(56) References Cited

U.S. PATENT DOCUMENTS 4,922,915 A * 5/1990 Arnold .................. A61B 6/583
                                                              378/18
5,467,404 A * 11/1995 Vuylsteke ............... G06T 5/007
                                                              382/128

(Continued)

OTHER PUBLICATIONS

Sung Ho Park et al., 2006, Evaluating Tone Mapping Algorithms for rendering Non-Pictorial (Scientific) High-Dynamic-Range Images, Rochester Institute of Technology, ACM Transactions on applied Perception, vol. V, No. N, Month 20YY, pp. 1-22.

(Continued)

*Primary Examiner* — Vu Le
*Assistant Examiner* — Aklilu Woldemariam
(74) *Attorney, Agent, or Firm* — Oblon, McClelland, Maier & Neustadt, L.L.P.

(57) ABSTRACT

An apparatus for image reconstruction is provided, including processing circuitry to obtain, from a scan of a region of interest of a patient, raw projection data of the region of interest; reconstruct the raw projection data to produce image data; apply high dynamic range tone-mapping to the image data to produce tone-mapped image data by applying window width and window level parameters to the image data to produce adjusted image data, and calculating a contrast adjustment based on both the image data and the adjusted image data; and quantize the tone-mapped image data to produce quantized tone-mapped image data for display.

12 Claims, 16 Drawing Sheets

(51) Int. Cl.
*G06T 5/20* (2006.01)
*G06T 11/00* (2006.01)
*G06T 11/60* (2006.01)

(52) U.S. Cl.
CPC ...... *G06K 9/00* (2013.01); *G06T 2207/10024* (2013.01); *G06T 2207/10081* (2013.01); *G06T 2207/20208* (2013.01); *G06T 2207/30061* (2013.01)

(58) Field of Classification Search
CPC ............. G06T 2207/30096; G06T 7/00; G06T 7/0014; G06T 2207/30004; G06T 2211/412; G06T 7/0016; G06T 7/0024; G06T 7/20; G06T 2207/20208; G06T 5/009; G06T 5/008; G06T 5/50; G06T 2207/20064; G06T 5/003; G06T 5/007; G06T 11/005; G06T 2207/10016; G06T 2207/10081; G06T 2207/20028; G06T 2207/30061; G06T 5/20; G06T 9/007; G06T 11/003; G06T 2207/30064; G06T 2207/30101; G06T 3/0006; G06T 3/20; G06T 7/0012; G06T 7/11; G06T 7/2006; G06T 7/215; G06K 2009/4666; G06K 2209/051; G06K 9/36; G06K 9/52; G06K 9/00; G01R 33/563
USPC ............... 382/128, 130, 131, 118, 232, 254; 600/407, 424, 431, 437
See application file for complete search history.

(56) References Cited

U.S. PATENT DOCUMENTS

| | | | | |
|---|---|---|---|---|
| 5,782,762 A * | 7/1998 | Vining | .................. | G06T 7/0012 128/920 |
| 6,275,721 B1 * | 8/2001 | Darrow | .................. | G01R 33/54 324/318 |
| 6,511,426 B1 * | 1/2003 | Hossack | .............. | A61B 8/5276 600/437 |
| 6,801,594 B1 * | 10/2004 | Ali | ........................ | A61B 6/032 378/114 |
| 7,072,707 B2 * | 7/2006 | Galloway, Jr. | ......... | A61B 90/36 600/407 |
| 7,787,927 B2 * | 8/2010 | Wood | ..................... | A61B 6/032 378/20 |
| 2001/0031920 A1 * | 10/2001 | Kaufman | ............... | A61B 5/055 600/431 |
| 2002/0057827 A1 * | 5/2002 | Nagata | .................... | G06T 5/009 382/131 |
| 2002/0181797 A1 * | 12/2002 | Young | .................... | G06T 5/004 382/260 |
| 2007/0103464 A1 * | 5/2007 | Kaufman | .............. | G06T 7/0012 345/424 |
| 2007/0276214 A1 * | 11/2007 | Dachille | ............... | G06T 7/0012 600/407 |
| 2009/0141854 A1 * | 6/2009 | Hirokawa | .............. | A61B 6/032 378/4 |
| 2010/0130860 A1 * | 5/2010 | Yamagata | .............. | A61B 8/483 600/443 |
| 2012/0008841 A1 * | 1/2012 | Johnson | .................. | G06T 19/00 382/131 |
| 2013/0315455 A1 * | 11/2013 | Wakai | .................. | A61B 6/5211 382/128 |
| 2015/0063669 A1 * | 3/2015 | Wiemker | ................ | G06T 15/08 382/131 |
| 2015/0085970 A1 * | 3/2015 | Bouhnik | .............. | A61B 6/4241 378/5 |

OTHER PUBLICATIONS

Takagi et al., Displaying a CT image about lung area and mediastinum area at same time, by applying a thresholding processing to a CT image about lung area, Japanese Society of Radiological Technology Kinki Branch, vol. 13, Series 3, Jan. 2008.

* cited by examiner

APPARATUS, METHOD, AND COMPUTER-READABLE MEDIUM FOR QUAD RECONSTRUCTION USING HYBRID FILTER CONVOLUTION AND HIGH DYNAMIC RANGE TONE-MAPPING

BACKGROUND

Field

Embodiments described herein relate to techniques for improving visibility in medical images.

Background

In many medical imaging modalities the dynamic range of acquired data exceeds the dynamic range of the device used for display, for example, Magnetic Resonance (MR) is 16 bit, Computed Tomography (CT) is 12 bit, and displays are 8 to 10 bits per channel. In most medical imaging applications, techniques known as Window & Leveling (or window width and window level) and color-mapping are used to control how an image is presented on the display.

The human visual system is very poor at determining the relative brightness of objects that are not adjacent. In the example shown in FIG. 1, the shade of gray of tiles A and B is exactly the same.

When a small window width is used to obtain good local contrast there will be areas of the image that are mapped outside of this range and will therefore be clamped to 100% black or 100% white, as shown in FIG. 2. This clamping hides information that is present in the original image data.

On the other hand, when a large window width is used it becomes more difficult to differentiate the boundaries between interesting structures, as shown in FIG. 3. This is because the boundaries are more likely to be mapped to similar gray levels. In these systems a particular data value is always mapped to a specific output color

BRIEF DESCRIPTION OF THE DRAWINGS

The disclosure will be better understood from reading the description which follows and from examining the accompanying figures. These figures are provided solely as non-limiting examples of the embodiments. In the drawings.

DETAILED DESCRIPTION

Figure 1:
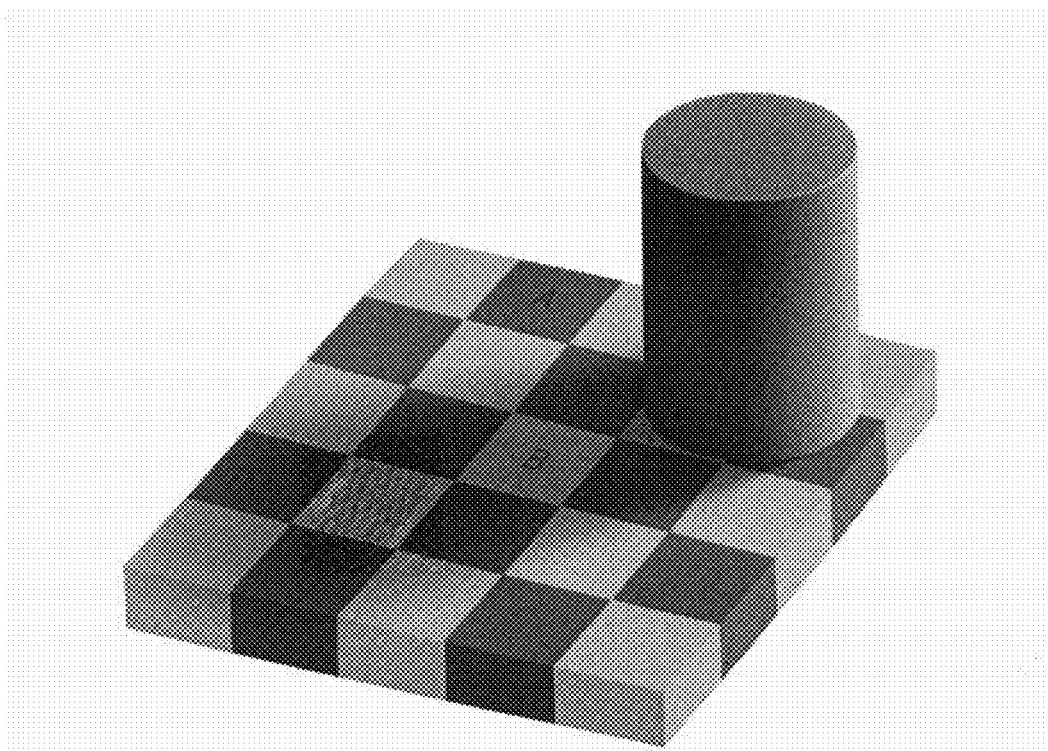
FIG. 1 illustrates tiles of shades of gray.
Figure 2:
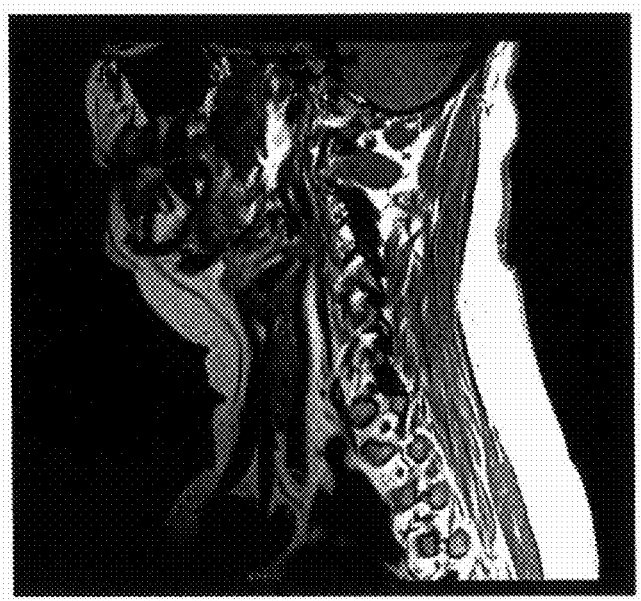
FIG. 2 illustrates an image having a narrow window width.
Figure 3:
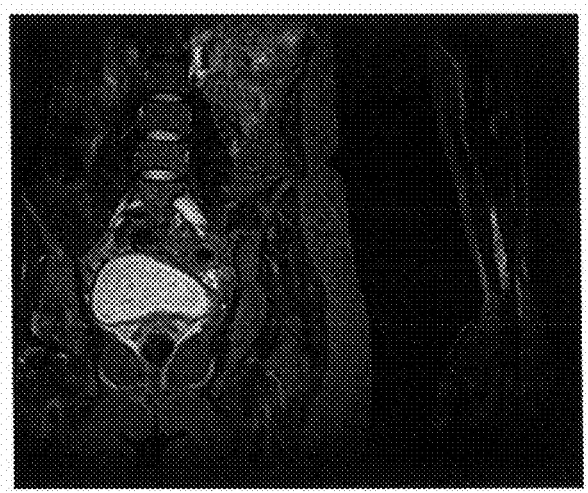
FIG. 3 illustrates an image having a wide window width.

The disclosed embodiments discuss an apparatus, a method, and a non-transitory computer-readable storage medium for image reconstruction.

In one embodiment, the apparatus comprises processing circuitry configured to obtain, from a scan of a region of interest of a patient, raw projection data of the region of interest; reconstruct the raw projection data to produce image data; apply high dynamic range tone-mapping to the image data to produce tone-mapped image data by applying window width and window level parameters to the image data to produce adjusted image data, and calculating a contrast adjustment based on both the image data and the adjusted image data; and quantize the tone-mapped image data to produce quantized tone-mapped image data for display.

In one embodiment, the processing circuitry is configured to reconstruct the raw projection data by performing a reconstruction of the raw projection data using a soft kernel to obtain first image data, extracting a tissue part from the first image data, applying an enhancing filter to the first image data to obtain second image data, extracting a lung part from the second image data, and superimposing the tissue part and the lung part to produce the image data.

In one embodiment, the processing circuitry is configured to reconstruct the raw projection data by performing a first reconstruction of the raw projection data using a soft kernel to obtain first image data, extracting a tissue part from the first image data, performing a second reconstruction of the raw projection data using a sharper kernel to obtain second image data, extracting a lung part from the second image data, and superimposing the tissue part and the lung part to produce the image data.

In one embodiment, the processing circuitry is further configured to receive input parameters and to calculate the contrast adjustment using the input parameters.

In one embodiment, the region of interest of the patient includes lungs and mediastinum, and the processing circuitry is further configured to display only the quantized tone-mapped image data, which displays both the lungs and the mediastinum.

In one embodiment, the processing circuitry is further configured to format the quantized tone-mapped image data into Digital Imaging and Communications in Medicine (DICOM) format.

In one embodiment, the method comprises obtaining, from a scan of a region of interest of a patient, raw projection data of the region of interest; reconstructing, by the processing circuitry, the raw projection data to produce image data; applying, by the processing circuitry, high dynamic range tone-mapping to the image data to produce tone-mapped image data by applying window width and window level parameters to the image data to produce adjusted image data, and calculating a contrast adjustment based on both the image data and the adjusted image data; and quantizing the tone-mapped image data to produce quantized tone-mapped image data for display.

In one embodiment, the reconstructing reconstructs the raw projection data by performing a reconstruction of the raw projection data using a soft kernel to obtain first image data, extracting a tissue part from the first image data, applying an enhancing filter to the first image data to obtain second image data, extracting a lung part from the second image data, and superimposing the tissue part and the lung part to produce the image data.

In one embodiment, the reconstructing reconstructs the raw projection data by performing a first reconstruction of the raw projection data using a soft kernel to obtain first image data, extracting a tissue part from the first image data, performing a second reconstruction of the raw projection data using a sharper kernel to obtain second image data, extracting a lung part from the second image data, and superimposing the tissue part and the lung part to produce the image data.

In one embodiment, the method further comprises receiving input parameters, wherein the calculating calculates the contrast adjustment using the input parameters.

In one embodiment, the method further comprises displaying only the quantized tone-mapped image data, which displays the region of interest of the patient, the region of interest of the patient including lungs and mediastinum.

In one embodiment, the method further comprises formatting the quantized tone-mapped image data into Digital Imaging and Communications in Medicine (DICOM) format.

In one embodiment, the non-transitory computer-readable storage medium includes computer executable instructions, wherein the instructions, when executed by a computer, cause the computer to perform a method for image reconstruction. The method comprising obtaining, from a scan of a region of interest of a patient, raw projection data of the region of interest; reconstructing the raw projection data to produce image data; applying high dynamic range tone-mapping to the image data to produce tone-mapped image data by applying window width and window level parameters to the image data to produce adjusted image data, and calculating a contrast adjustment based on both the image data and the adjusted image data; and quantizing the tone-mapped image data to produce quantized tone-mapped image data for display.

In one embodiment, the reconstructing reconstructs the raw projection data by performing a reconstruction of the raw projection data using a soft kernel to obtain first image data, extracting a tissue part from the first image data, applying an enhancing filter to the first image data to obtain second image data, extracting a lung part from the second image data, and superimposing the tissue part and the lung part to produce the image data.

In one embodiment, the reconstructing reconstructs the raw projection data by performing a first reconstruction of the raw projection data using a soft kernel to obtain first image data, extracting a tissue part from the first image data, performing a second reconstruction of the raw projection data using a sharper kernel to obtain second image data, extracting a lung part from the second image data, and superimposing the tissue part and the lung part to produce the image data.

In one embodiment, the non-transitory computer-readable storage medium further comprises receiving input parameters, wherein the calculating calculates the contrast adjustment using the input parameters.

In one embodiment, the non-transitory computer-readable storage medium further comprises displaying only the quantized tone-mapped image data, which displays the region of interest of the patient, the region of interest of the patient including lungs and mediastinum.

In one embodiment, the non-transitory computer-readable storage medium further comprises formatting the quantized tone-mapped image data into Digital Imaging and Communications in Medicine (DICOM) format.

Embodiments of the present disclosure are directed to preparing an image for display by using tone-mapping and incorporating the existing window-and-level and color-mapping stages.

To briefly summarize, the window width and window level or color-mapping is applied first. Window and leveling can be thought of as a specific case of color mapping where there are only two (2) gray-scale colors. More complex color mappings are also sometimes used.

Color-mapping (also called tone-mapping) can be used to apply color transformations on the final image colors. Color-mapping is a function that maps (or transforms) the colors of one image to the colors of another image. For example, an image may contain a higher range of colors than can be displayed on a computer screen. Thus, the color-mapping technique re-maps the image values to be suitable for particular display purposes.

Window width refers to the range of CT numbers (in Hounsfield units) included in the gray-scale video display of a CT image, ranging from 1 to 2000 or 3000, depending on the type of machine. For example, a typical window width for imaging the lungs is 1500, and for imaging the mediastinum is 400.

In other words, window width refers to the number of shades of gray in an image and controls image contrast. A wide window represents low contrast in an image.

Window level refers to the CT number setting in Hounsfield units of the midpoint of the window width, which is the gray-scale of the image. The window level controls brightness of the image. For example, a typical window level for imaging the lungs is −500, and for imaging the mediastinum is 40.

Next, the original source image and the new post window and level or color map image are used to calculate adjustment factors. Over-exposed areas are then attenuated and under-exposed areas are amplified to make the structures in these areas visible.

There are many local contrast adjustment operators that can be used as part of the present embodiments. These have been developed to perform tone-mapping of High Dynamic Range (HDR) Imaging systems, which solve a similar problem in the photographic imaging domain.

Figure 4:
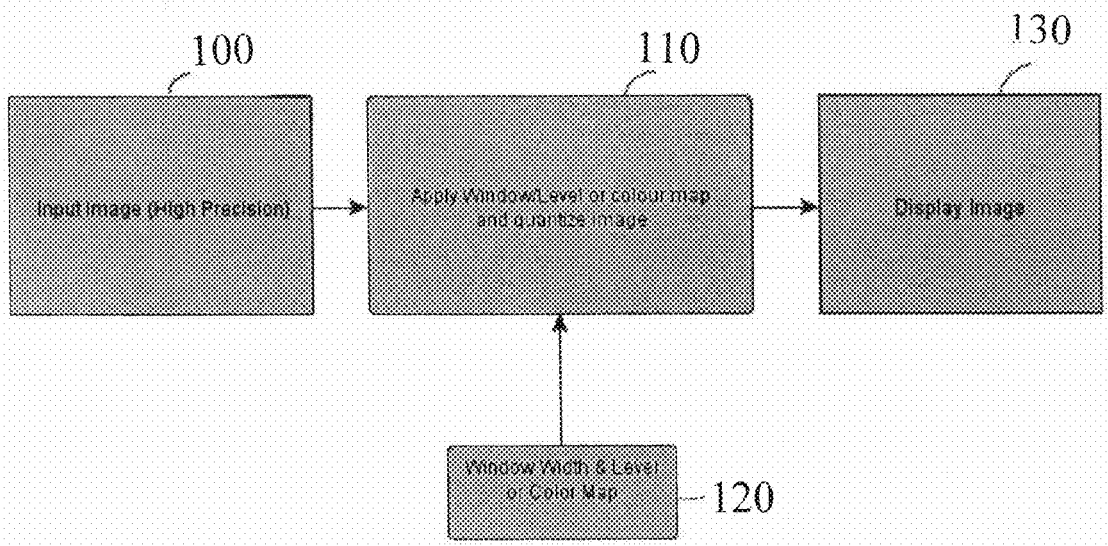
FIG. 4 illustrates a process of medical imaging applications.

FIG. 4 illustrates a typical process of medical imaging applications. As shown in FIG. 4, an original high precision image is acquired at block 100, and, at block 110, window width and window level or color map parameters are applied to the original image, and the image is quantized. The window width and level or color map parameters are input, for example, by an operator, at block 120. At block 130, the quantized image is displayed.

Figure 5:
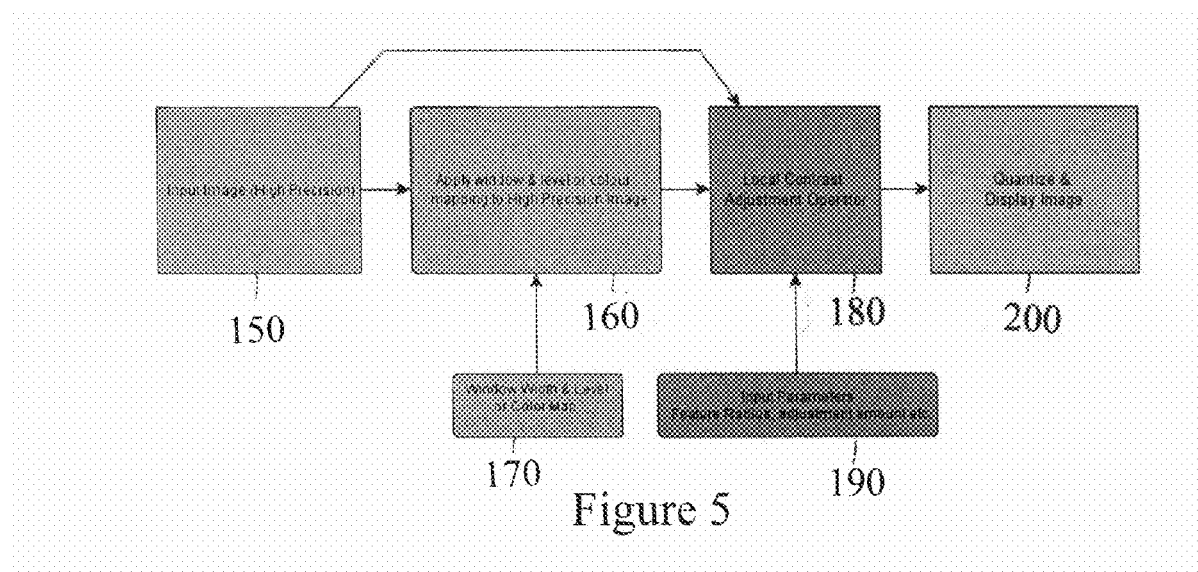
FIG. 5 illustrates a process of medical imaging applications according to an embodiment.

FIG. 5 shows a process of medical imaging applications according to one embodiment of the present disclosure. As shown in FIG. 5, an original high precision image is acquired at block 150, and, in block 160, window width and window level or color map parameters are applied to the original image. In one embodiment, the window width and level or color map parameters are input, for example, by an operator, at block 170.

In one embodiment, the parameters are input and stored, in a memory, by the operator for future use. Thus, at block 170, the operator can use previously stored parameters. The parameters are based upon the particular task. Each task can be assigned a parameter setting that would be displayed through the images.

Next, at block 180, an optimal local contrast adjustment is calculated based on both the original image output from block 150 and the windowed-and-leveled or color-mapped image output from block 160. In particular, at block 180, existing HDR tone mapping filters are used on the original image to identify the amount of exposure correction needed at each pixel in the window-leveled or color mapped image.

The aforementioned calculation at block 180 is performed using input parameters such as feature radius, adjustment amount, etc., which are input at block 190. These parameters affect the strength of the exposure correction and the size of the features that the adjustment will affect. The adjustability of the contrast and size of the locality kernel is performed based on the specific use cases. The settings can be tuned to adapt the algorithm (the process of FIG. 5) to work with data from different scan protocols and different scanner resolutions. Finally, at block 200, the image from block 180 is quantized and displayed.

Figure 6:
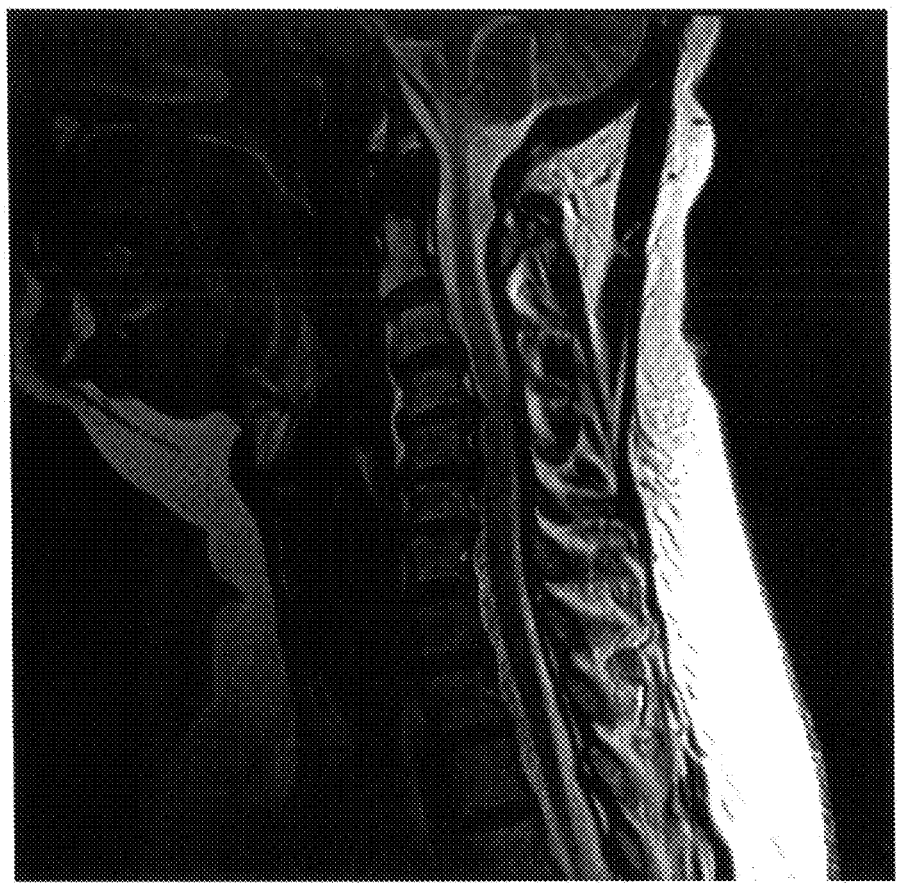
FIG. 6 illustrates an image resulting from using the process of FIG. 4 in which only window and level is applied.
Figure 7:
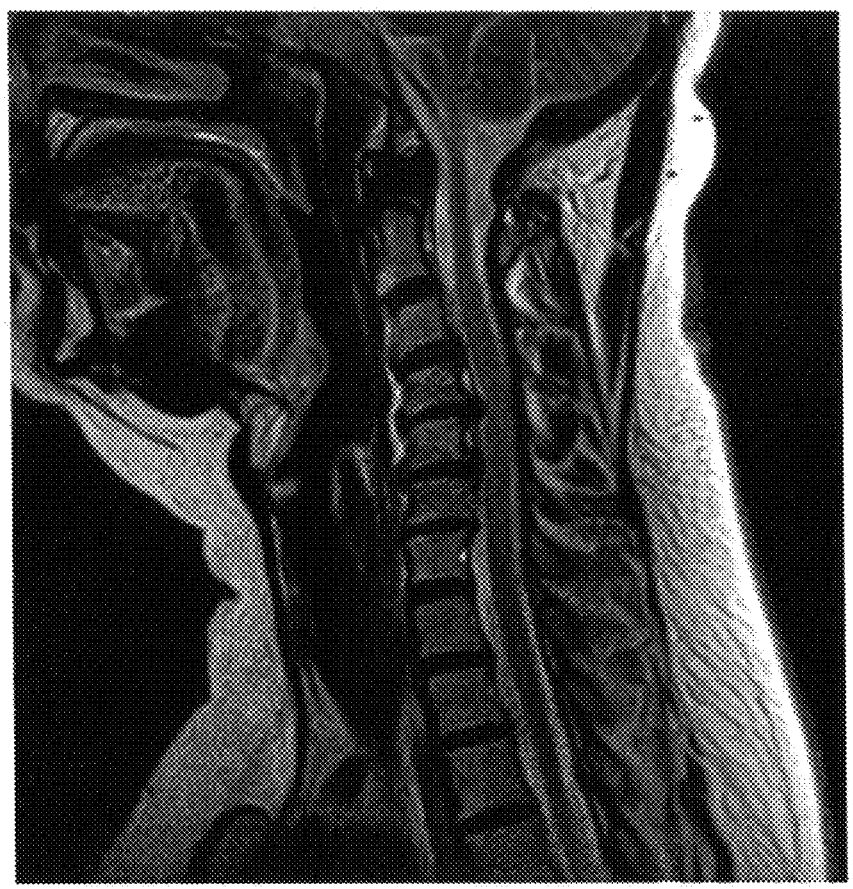
FIG. 7 illustrates an example of an image resulting from using the process of FIG. 5 in which both window and level and local contrast adjustment are applied.

FIG. 6 shows an example of an image resulting from using the process of FIG. 4 in which only window width-and-level is applied. On the other hand, FIG. 7 shows an example of an image resulting from using the process of FIG. 5 in which both window width and level and local contrast adjustment are applied.

Figure 8:
FIG. 8 illustrates an example of an image resulting from using the process of FIG. 4 in which only window and level is applied.
Figure 9:
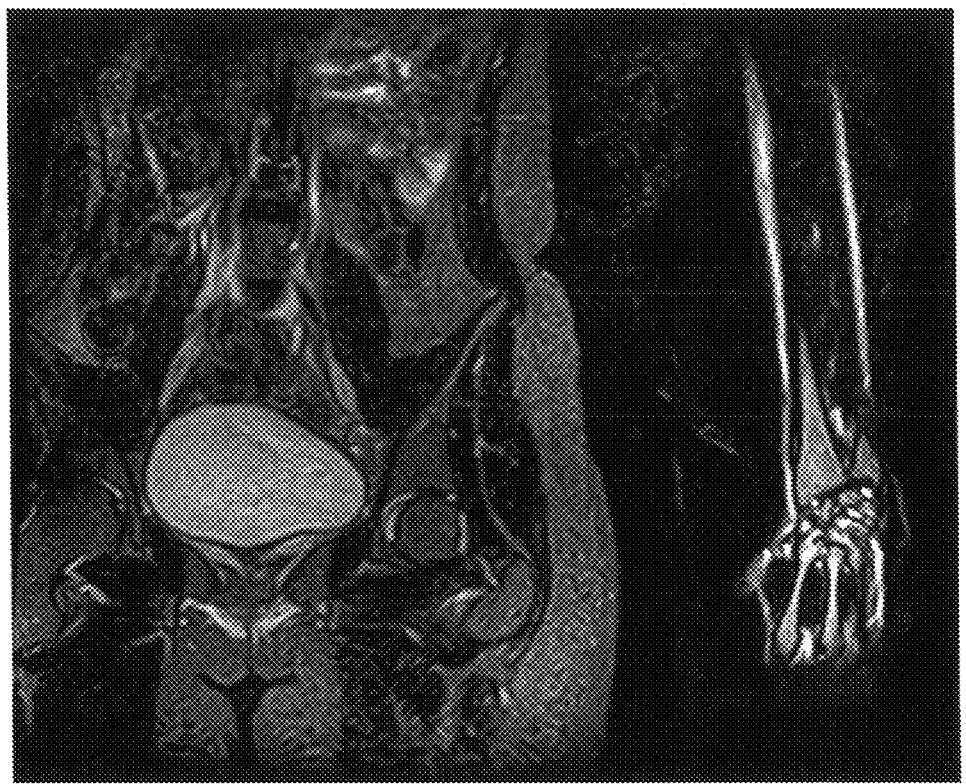
FIG. 9 illustrates an example of an image resulting from using the process of FIG. 5 in which both window and level and local contrast adjustment are applied.

Similarly to FIG. 6, FIG. 8 shows an example of an image resulting from using the process of FIG. 4 in which only window width-and-level is applied. Similar to FIG. 7, FIG. 9 shows an example of an image resulting from using the process of FIG. 5 in which both window width and level and local contrast adjustment are applied.

The process of FIG. 5 sets forth various advantages over the process of FIG. 4. As can be seen by comparing FIG. 6 with FIG. 7 and FIG. 8 with FIG. 9, in FIGS. 7 and 9 more structures are visible in each of the images. In one embodiment, the process of FIG. 5 increases the probability that an abnormality is spotted during a review of slices.

In one embodiment, the process of FIG. 5 reduces reconstruction time on the image acquisition system. In one embodiment, the process of FIG. 5 reduces transfer time from the image acquisition system to a Picture Archiving and Communication System (PACS) or Digital Imaging and Communications in Medicine (DICOM) workstation with one data set. The PACS is a system that handles DICOM and secondary capture images from various medical imaging instruments including, but not limited to, MR, CT, and Positron Emission Tomography (PET). In one embodiment, the process of FIG. 5 reduces storage commitment on the PACS. In one embodiment, the process of FIG. 5 reduces viewing and reporting time.

Further, in one embodiment, the process of FIG. 5 can improve reading confidence by evaluating all structures together. For example, correlative analysis between lung and mediastinum can be performed together without the need to link two separately reconstructed data sets together.

Moreover, using the original data to control the contrast adjustment avoids cases where the color map or window level setting maps many different values to a single color or intensity. In this case, it would otherwise not be possible to make the original structure visible. If many values are mapped to a single color, it is then impossible to go backwards from that single color to the correct original sample value.

Further, in one embodiment, the process of FIG. 5 can reduce the number of passes needed to read a study at different window level settings.

The processes discussed above may be used in various applications. In one embodiment, the process of FIG. 5 may be used during review of two-dimensional (2D) slices, Multi-Planar Reformatting (MPR), and slab images on a scanner console or advanced visualization application. In one embodiment, the process of FIG. 5 may be combined with histogram analysis to determine initial window-and-level settings to give better default viewing parameters for Magnetic Resonance (MR). Thus, patterns can be identified in the histogram to identify appropriate initial window and level settings.

In one embodiment, the process of FIG. 5 may also be applied to CT. Additionally, aside from medical diagnosis, the process of FIG. 5 is beneficial for communication and presentation tasks.

Traditional CT brain imaging requires two reconstruction kernels: (1) low frequency for brain tissue structure, and (2) high frequency for cranium. Traditional CT brain imaging also requires two window width and window level settings: (1) narrow window width and level for brain structure, and (2) wide window width and level for bone structure visualization.

Traditional CT chest imaging requires two reconstruction kernels: 1) low frequency for mediastinal structure, and 2) high frequency for lung parenchyma. Traditional CT chest imaging also requires two window width and window level settings: (1) narrow window width and level for mediastinal structure, and (2) wide window width and level for lung parenchyma. Typically, only one kernel is used for the task of viewing a particular structure. The number assigned to the kernel or filter convolution or convolution is vendor dependent.

Even though two data sets are acceptable practice, there is an increase in clinical reporting time (to review two data sets separately and perform correlative analysis between both data sets), and an increase in archival space on PACS.

Figure 10:
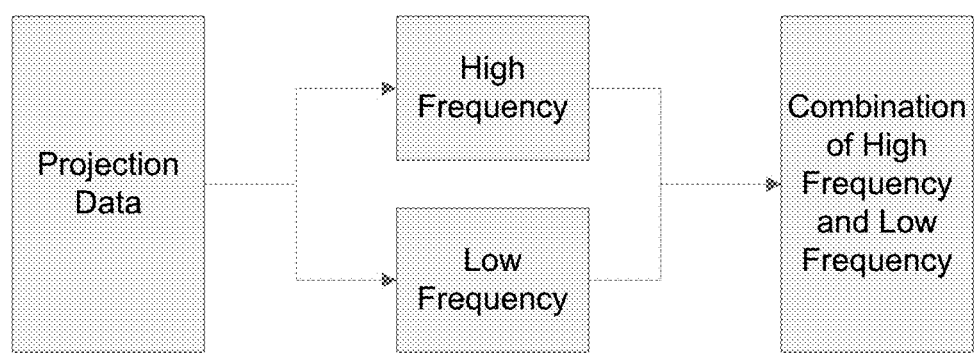
FIG. 10 illustrates a process of a hybrid filter convolution technique according to an embodiment.

FIG. 10 illustrates a hybrid filter convolution technique. The proposed solution is to combine the HDR tone-mapping discussed above with the hybrid filter convolution technique (illustrated in FIG. 10) to provide all frequency and window solutions in (only) one data set such as CT chest image reconstruction or routine brain image reconstruction for diagnostic reading. In one embodiment, the hybrid filter convolution technique is a composite scan of two or more reconstructions blended together.

FIG. 11 shows an example of imaging lungs using the process of FIG. 10. FIG. 11A shows an image of the lungs with a high-pass filter convolution, and FIG. 11B shows an image of the mediastinum with a low-pass filter convolution.

Figure 11A:
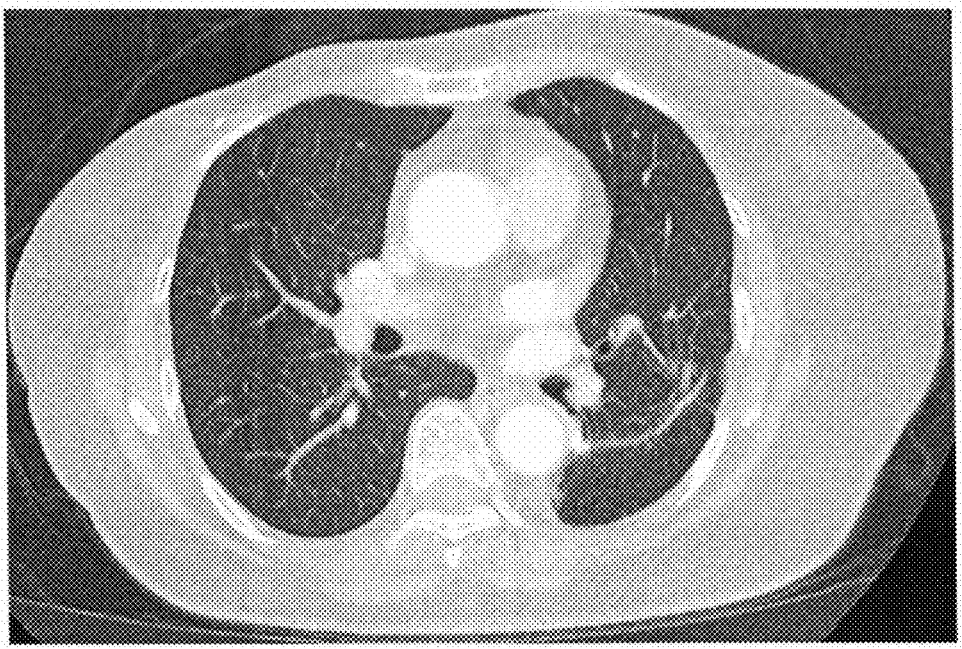
FIG. 11A illustrates an image of the lungs with a high-pass filter convolution being displayed with a representation of a lung window width and level.
Figure 11B:
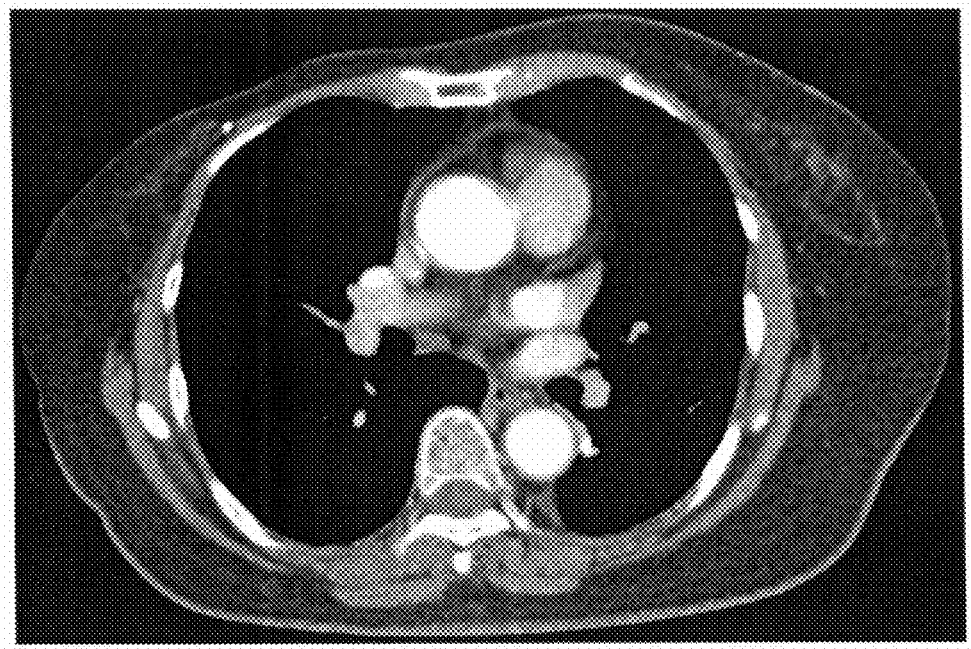
FIG. 11B illustrates an image of the mediastinum with a low-pass filter convolution being displayed with a representation of a soft tissue window width and level.
Figure 11C:
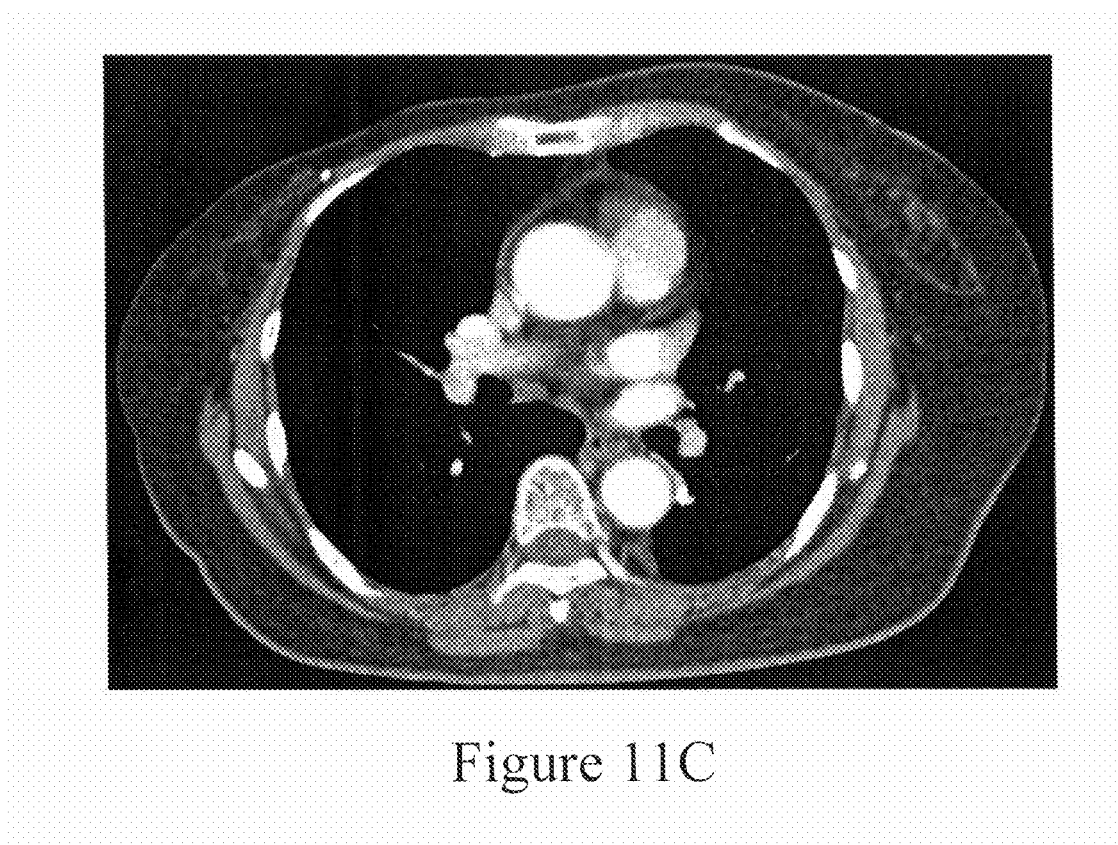
FIG. 11C illustrates an image that is a combination of the images of FIGS. 11A and 11B being displayed with a representation of a soft tissue window width and level.
Figure 11D:
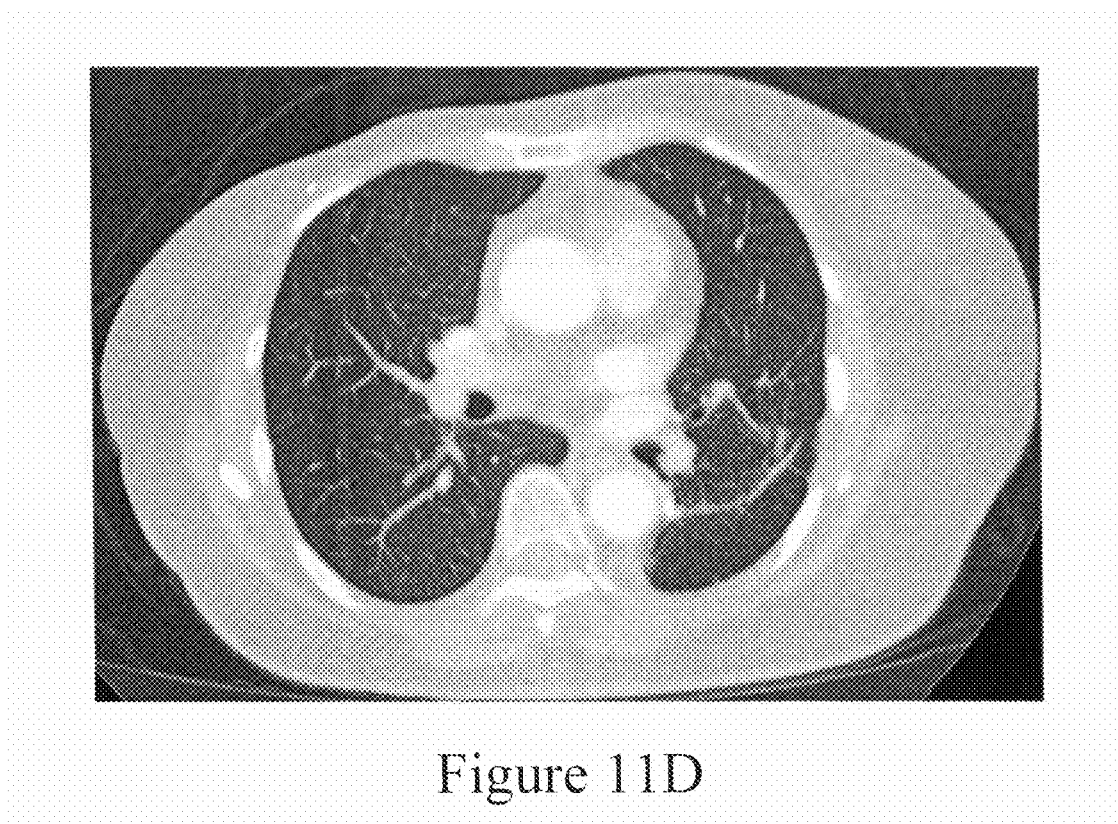
FIG. 11D illustrates an image that is a combination of the images of FIGS. 11A and 11B being displayed with a representation of a lung window width and level.

FIG. 11C illustrates an image (having been generated with hybrid filter convolution) that is a combination of the images in FIGS. 11A and 11B being displayed with a representation of a soft tissue window width and level. FIG. 11D illustrates an image (having been generated with hybrid filter convolution) that is a combination of the images in FIGS. 11A and 11B being displayed with a representation of a lung window width and level.

Figure 11E:
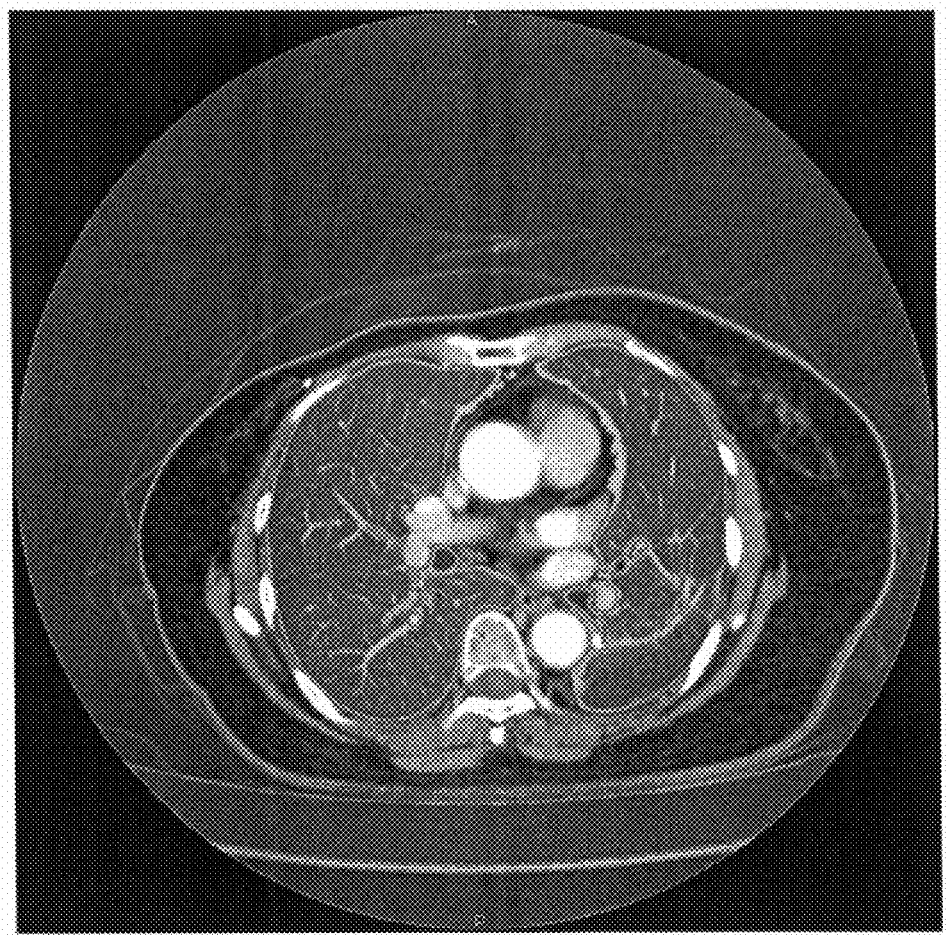
FIG. 11E illustrates an image that is a combination of the images in FIGS. 11A and 11B.

FIG. 11E is an image that shows the combination of the images in FIGS. 11A and 11B, having been generated with hybrid filter convolution (which includes both the high-pass and low-pass filter convolution) and finally applying HDR tone-mapping. As can be seen from the image shown in FIG. 11E, both the high frequency lungs and the low frequency mediastinum are visible simultaneously.

Figure 12:
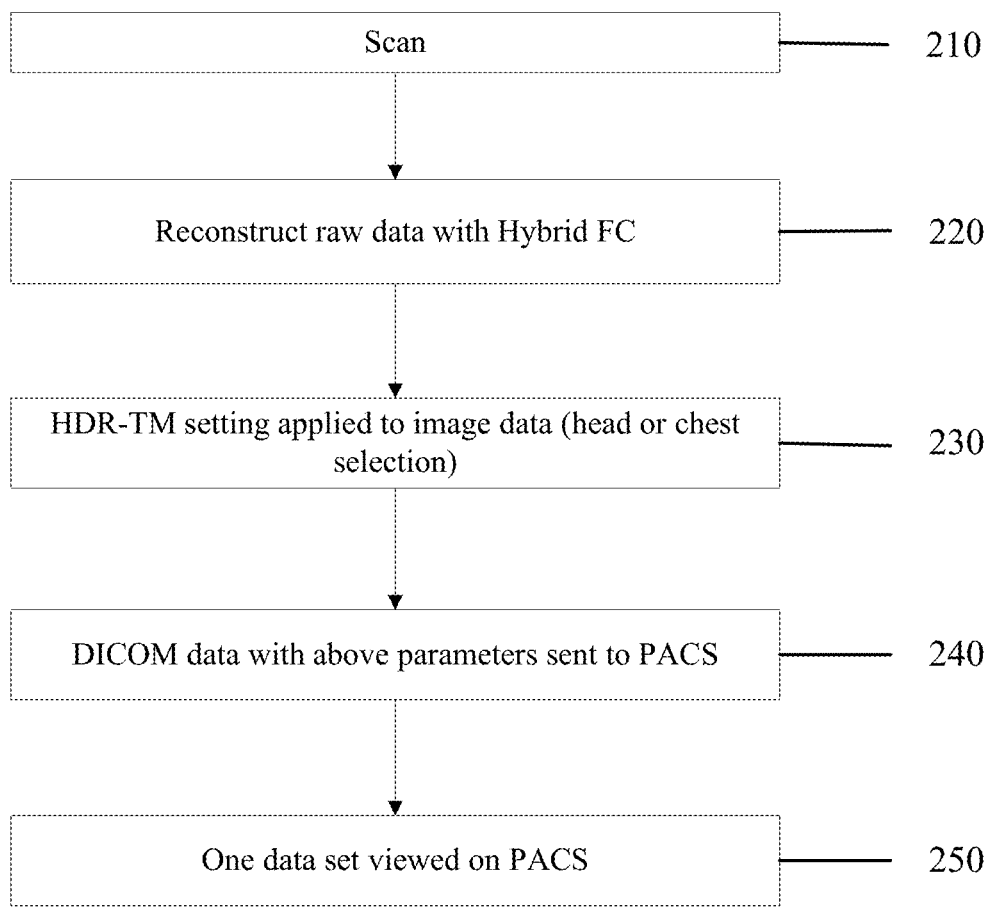
FIG. 12 illustrates a process of generating the image shown in FIG. 11E according to an embodiment.

FIG. 12 shows an embodiment of the process of generating the image shown in FIG. 11E. The following process may be applied to the head area and/or the chest area of a patient. First, at block 210, a scan is performed of the area/region of interest (for example, head, chest, etc.) of the patient, and the raw data obtained from the scan is reconstructed with the hybrid filter convolution (high-pass and low-pass filter convolution), at block 220, to obtain image data that is a combination of both filter convolutions.

In one embodiment, a method of achieving the hybrid convolution, at block 220, is to perform reconstruction once with a soft kernel and then to apply an enhance filter in the image domain, as follows. First, reconstruction is performed of the raw data obtained from the scan at block 210, with a soft kernel to obtain first image data. Then, a tissue part (for example, of the mediastina) is extracted in the image domain from the first image data. The outcome is shown in FIG. 11B. Next, an enhancing filter is applied in the image domain to the first image data to obtain second image data, and a lung part (lung parenchyma) is extracted from the second image data in the image domain. The outcome is shown in FIG. 11A. Finally, the two aforementioned results are superimposed to achieve the outcome (hybrid filter convolution) shown in FIG. 11A and FIG. 11B. Note that FIGS. 11C and 11D do not represent an intermediate step to achieve the result illustrated in FIG. 11E. Rather, FIGS. 11C and 11D are used to illustrate a superimposition of FIGS. 11A and 11B with different window widths and levels.

In another embodiment, a method of achieving the hybrid convolution, at block 220, is to perform reconstruction twice, as follows. A first reconstruction is performed of the raw data obtained from the scan at block 210, with a soft or low frequency kernel to obtain first image data, and a tissue part (for example, of the mediastina) is extracted from the first image data. The outcome is shown in FIG. 11B. A second reconstruction is performed of the raw data obtained from the scan at block 210, with a sharper kernel to obtain second image data, and a lung part (lung parenchyma) is extracted from the second image data. The outcome is shown in FIG. 11A. Finally, the two aforementioned results are superimposed to achieve the outcome (hybrid filter convolution) shown in FIG. 11A and FIG. 11B. Note that in the present disclosure, the low-pass, the low frequency, the soft kernel, and the smooth filter are the same and thus used interchangeably. Further, the high-pass, the high frequency, the sharper kernel, and the enhance filter are the same and thus used interchangeably.

Next, at block 230, HDR tone-mapping is applied to the hybrid filter convolution image data generated at block 220 using the process discussed above with respect to FIG. 5. In particular, window width and window level or color map parameters are applied to the hybrid filter convolution image data. In one embodiment, such window width and level or color map parameters are input, for example, by an operator. In one embodiment, the parameters may be input by the operator, as discussed above.

Next, an optimal local contrast adjustment is calculated based on both the hybrid filter convolution image data and the window width/level or color-mapped hybrid filter convolution image data. The aforementioned calculation is performed using input parameters feature radius, adjustment amount, etc. The adjustability of the contrast and size of locality kernel is performed based on the specific use cases. The signal to noise ratio, the size of features to pixel dimension ratio, and the dynamic range of the original scan data will affect the choice of parameters for the contrast adjustment.

Finally, the image data thus produced is quantized and formatted in the DICOM format (which is a standard for handling, storing, printing, and transmitting information in medical imaging). At block 240, the DICOM formatted image data is sent to the PACS. At block 250, the PACS displays the one data set at block 250. The one data set shows all anatomical structures. Following the example in FIG. 11E, with the aforementioned process, both the lungs and mediastinum are visible in the image.

The process discussed above with respect to FIG. 12 may be built into the reconstruction chain on, for example, Toshiba's Aquilion console (a CT system) to include the HDR tone-mapping in addition to a traditional window width/window level display option, making the process seamless and automatic. The reconstructed data may be then directly exported to a reading station, such as PACS.

In one embodiment, the HDR tone-mapping may be accessed via a switch, which allows the feature to be turned on and off completely. In one embodiment, a slider that controls the strength of the algorithm can also be included. The slider may control either a parameter in the dynamic range adjustment algorithm or control a weighted blend between the original window leveled image and the processed image.

Figure 13:
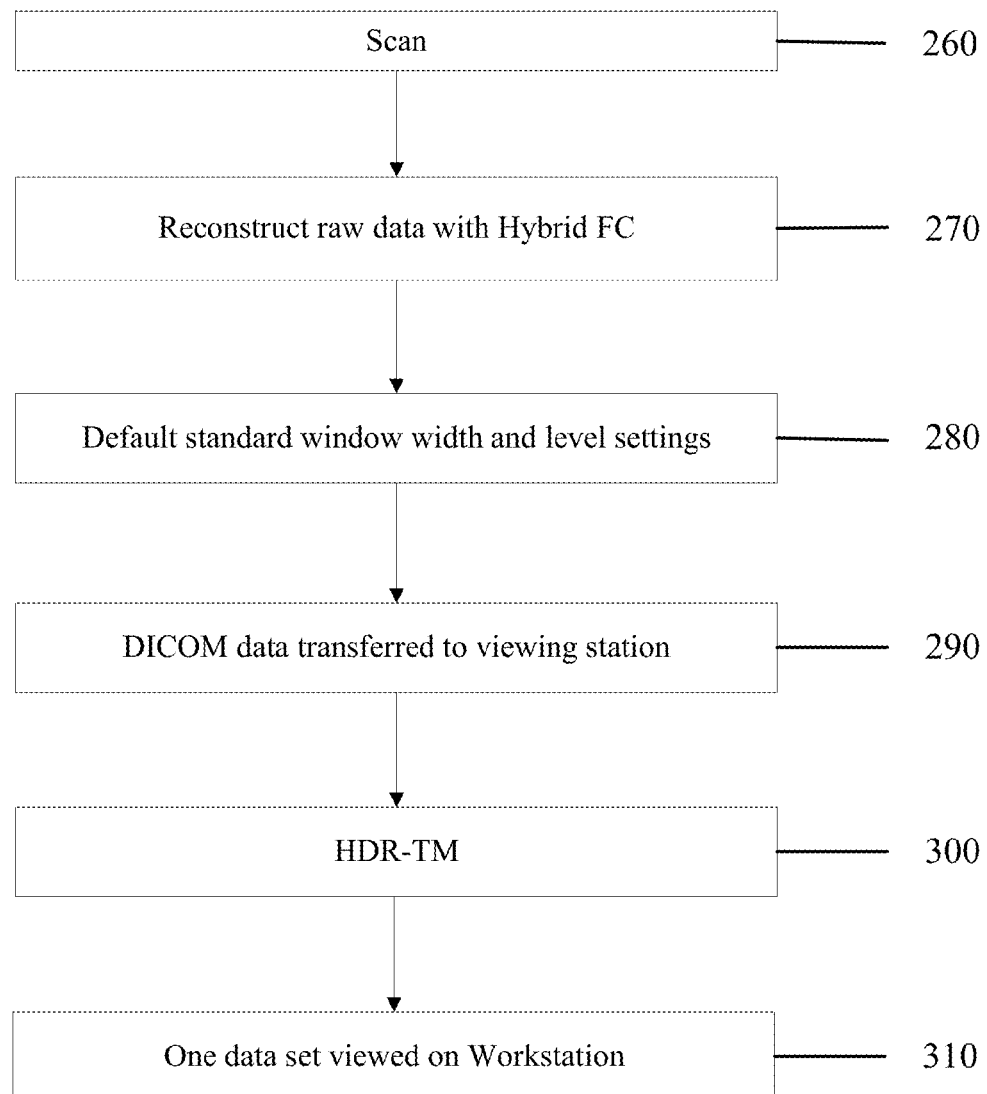
FIG. 13 illustrates a process of generating the image shown in FIG. 11E according to an embodiment.

FIG. 13 shows another embodiment of the process of generating the image shown in FIG. 11E. First, at block 260, a scan is performed, and the raw data obtained from the scan is reconstructed with the hybrid filter convolution, at block 270. Similarly to block 220 of FIG. 12, at block 270, high-pass and low-pass filter convolution is applied to the data obtained by the scan (projection data) to obtain image data that is a combination of both filter convolutions.

Next, at block 280, default standard window width and level settings are applied to the hybrid filter convolution image data generated at block 270. In one embodiment, the default settings can be a window width of 1600 and window level of −400 for the lung. In one embodiment, the default settings can be a window width of 90 and a window level of 40 for the brain.

The image data from block 280, which is in the DICOM format, is transferred to a viewing station, as shown in block 290. At block 300, HDR tone-mapping setting is applied. The settings will be tuned to particular use cases or to particular scanning protocols. Next, at block 310, the (only) one data set is displayed.

In one embodiment, the hybrid filter convolution process (block 270) may be a part of the processing chain of the scanner (for example, a CT scanner). In one embodiment, the HDR tone-mapping process may reside on a PACS archival viewing station, a cloud-based DICOM image workstation, or a hardware-based DICOM image workstation.

The processes discussed above, for example, with respect to FIGS. 12 and 13 provide various advantages over conventional processes. For example, the processes of the present disclosure reduce reconstruction and transfer time to (only) one data set, as well as reduce storage capacity. Viewing and reporting on one data set reduces reporting time and improves reading confidence by evaluating all structures (for example, the lungs and mediastinum, as shown in FIG. 11E) together. Thus, correlative analysis between, for example, the lungs and mediastinum can be performed without the need to link two data sets together.

Each of the functions described above may be implemented by one or more processing circuits. A processing circuit includes a programmed processor (for example, processor 1203), as a processor includes circuitry. A processing circuit also includes devices such as an application specific integrated circuit (ASIC) and conventional circuit components arranged to perform the recited functions.

Figure 14:
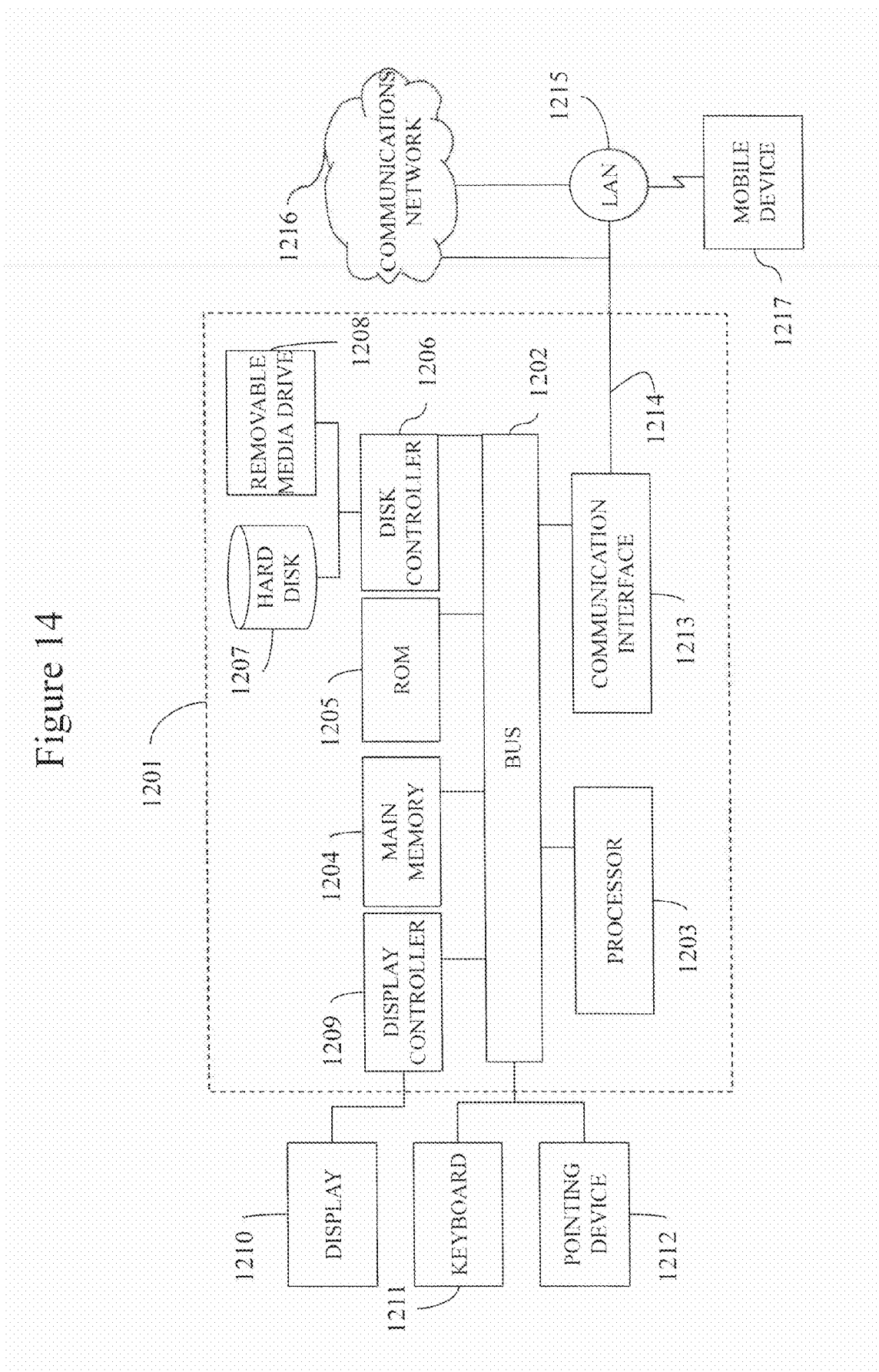
FIG. 14 illustrates a computer system upon which disclosed embodiments may be implemented.

Further, the process discussed in the disclosed embodiments can be performed by a CT system or a computer system (or programmable logic). FIG. 14 illustrates a computer system 1201 upon which disclosed embodiments may be implemented. The computer system 1201 may perform the above-described processes (for example, the processes discussed with respect to FIGS. 4, 5, 10, 12, and 13) and communicate with a CT system.

The computer system 1201 includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, for displaying information to a computer user. The computer system includes input devices, such as a keyboard 1211 and a pointing device 1212, for interacting with a computer user and providing information to the processor 1203. The pointing device 1212, for example, may be a mouse, a trackball, a finger for a touch screen sensor, or a pointing stick for communicating direction information and command selections to the processor 1203 and for controlling cursor movement on the display 1210.

The processor 1203 executes one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1201, for driving a device or devices for implementing the invention, and for enabling the computer system 1201 to interact with a human user. Such software may include, but is not limited to, device drivers, operating systems, and applications software. Such computer readable media further includes the computer program product of the present disclosure for performing all or a portion (if processing is distributed) of the processing performed in implementing the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1203 for execution. A computer readable medium may take many forms, including but not limited to, non-volatile media or volatile media. Non-volatile media includes, for example, optical, magnetic disks, and magneto-optical disks, such as the hard disk 1207 or the removable media drive 1208. Volatile media includes dynamic memory, such as the main memory 1204. Transmission media, on the contrary, includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1201 may receive the data on the telephone line and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an integrated services digital network (ISDN) card. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc.). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone.

The present embodiments described above provide improvements of conventional imaging and display techniques.

For example, the document reference *Displaying a CT image about lung area and mediastinum area at same time, by applying a thresholding processing to a CT image about lung area*, (Japanese Society of Radiological Technology Kinki Branch, Vol. 13, Series 3, January, 2008) is concerned with displaying the lung area and the mediastinum area at a same time with different window-levels, by using different reconstruction kernels and a computer-aided diagnostic (CAD) extracting technique for cutting out the lung area from the CT image. In particular, this reference discusses generating raw projection data about the chest area with contrast, and then reconstructing a lung area image and a mediastinum area image separately. Next, an air region outside the subject is removed from the images, and an air region inside the subject is extracted from the images.

Next, an area with a high CT value inside the lung area is extracted and then the extracted lung area is displayed with different window width and window level parameter from the original images. Finally, this extracted lung area with different window width and window level parameter is superimposed on the original mediastinum area image.

However, the image kernels that demonstrate the low frequency for soft tissue and the high frequency for lung parenchyma tissue are not implemented by this reference. In fact, in the aforementioned reference, only one frequency can be applied at a time. Thus, in the aforementioned reference, two frequencies (low and high) cannot be simultaneously applied, as is discussed in the embodiments presented in the present disclosure.

U.S. Patent Publication No. 2002/0057827 to Nagata et al. discusses tomographic image processing that enables lung areas and a mediastinum in a chest tomographic image to be reproduced in one image with appropriate contrast. This reference also uses frequency enhancing to minimize the blurring effect of the dynamic range compression.

However, such a technique will not provide as good image quality (for example, in the lung regions) as the techniques discussed in the embodiments presented in the present disclosure. Even using selective sharpening in the lung region from a single scan reconstructed with a mediastinum kernel is inferior to applying two frequencies simultaneously, as is the case in the embodiments of the present disclosure.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An apparatus for image reconstruction, comprising:
processing circuitry configured to obtain, from a scan of a region of interest of a patient, raw projection data of the region of interest, reconstruct the raw projection data to produce image data, apply high dynamic range tone-mapping to the image data to produce tone-mapped image data by applying window width and window level parameters to the image data to produce adjusted image data, and
calculating a contrast adjustment based on both the image data and the adjusted image data, and
quantize the tone-mapped image data to produce quantized tone-mapped image data for display, wherein the processing circuitry is configured to reconstruct the raw projection data by performing a first reconstruction of the raw projection data using a soft kernel to obtain first image data, extracting a tissue part from the first image data,
performing a second reconstruction of the raw projection data using a sharper kernel to obtain second image data, extracting a lung part or a brain part from the second image data, and superimposing the tissue part and the lung part or the brain part to produce the image data.

2. The apparatus according to claim 1, wherein
the processing circuitry is further configured to receive input parameters and to calculate the contrast adjustment using the input parameters.

3. The apparatus according to claim 1, wherein
the region of interest of the patient includes lungs and mediastinum, and
the processing circuitry is further configured to display only the quantized tone-mapped image data, which displays both the lungs and the mediastinum.

4. A method for image reconstruction implemented by an apparatus including processing circuitry, the method comprising:
obtaining, from a scan of a region of interest of a patient, raw projection data of the region of interest;

reconstructing, by the processing circuitry, the raw projection data to produce image data;
applying, by the processing circuitry, high dynamic range tone-mapping to the image data to produce tone-mapped image data by applying window width and window level parameters to the image data to produce adjusted image data, and calculating a contrast adjustment based on both the image data and the adjusted image data; and
quantizing the tone-mapped image data to produce quantized tone-mapped image data for display, wherein the reconstructing reconstructs the raw projection data by performing a first reconstruction of the raw projection data using a soft kernel to obtain first image data, extracting a tissue part from the first image data, performing a second reconstruction of the raw projection data using a sharper kernel to obtain second image data, extracting a lung part or a brain part from the second image data, and superimposing the tissue part and the lung part or the brain part to produce the image data.

5. The method according to claim 4, further comprising:
receiving input parameters, wherein
the calculating calculates the contrast adjustment using the input parameters.

6. The method according to claim 4, further comprising:
displaying only the quantized tone-mapped image data, which displays the region of interest of the patient, the region of interest of the patient including lungs and mediastinum.

7. A non-transitory computer-readable storage medium including computer executable instructions, wherein the instructions, when executed by a computer, cause the computer to perform a method for image reconstruction, the method comprising:
obtaining, from a scan of a region of interest of a patient, raw projection data of the region of interest;
reconstructing the raw projection data to produce image data;
applying high dynamic range tone-mapping to the image data to produce tone-mapped image data by applying window width and window level parameters to the image data to produce adjusted image data, and calculating a contrast adjustment based on both the image data and the adjusted image data; and
quantizing the tone-mapped image data to produce quantized tone-mapped image data for display, wherein the reconstructing reconstructs the raw projection data by performing a first reconstruction of the raw projection data using a soft kernel to obtain first image data, extracting a tissue part from the first image data, performing a second reconstruction of the raw projection data using a sharper kernel to obtain second image data, extracting a lung part or a brain part from the second image data, and superimposing the tissue part and the lung part or the brain part to produce the image data.

8. The non-transitory computer-readable storage medium according to claim 7, further comprising:
receiving input parameters, wherein
the calculating calculates the contrast adjustment using the input parameters.

9. The non-transitory computer-readable storage medium according to claim 7, further comprising:
displaying only the quantized tone-mapped image data, which displays the region of interest of the patient, the region of interest of the patient including lungs and mediastinum.

10. The apparatus according to claim 1, wherein the processing circuitry is further configured to
format the quantized tone-mapped image data into Digital Imaging and Communications in Medicine (DICOM) format, and
transmit the DICOM formatted image data to a reading station.

11. The method according to claim 4, further comprising:
formatting the quantized tone-mapped image data into Digital Imaging and Communications in Medicine (DICOM) format; and
transmitting the DICOM formatted image data to a reading station.

12. The non-transitory computer-readable storage medium according to claim 7, further comprising:
formatting the quantized tone-mapped image data into Digital Imaging and Communications in Medicine (DICOM) format; and
transmitting the DICOM formatted image data to a reading station.

* * * * *